United States Patent [19]

Geltosky

[11] Patent Number: 4,524,025

[45] Date of Patent: Jun. 18, 1985

[54] HYBRIDOMA CELL LINES AND MONOCLONAL ANTIBODIES TO THEOPHYLLINE

[75] Inventor: John E. Geltosky, Hockessin, Del.

[73] Assignee: E. I. Du Pont de Nemours and Company, Wilmington, Del.

[21] Appl. No.: 406,554

[22] Filed: Aug. 9, 1982

Related U.S. Application Data

[63] Continuation-in-part of Ser. No. 393,680, Jun. 30, 1982, abandoned.

[51] Int. Cl.$^3$ .................. A23J 1/00; C12P 21/00; C12N 5/00; G01N 33/54
[52] U.S. Cl. .................. 260/112 R; 435/7; 435/68; 435/240; 435/948; 436/548; 424/85; 260/112 B
[58] Field of Search .............. 436/500, 548, 531; 424/85; 435/68, 7, 240, 241, 41, 948; 260/112 R, 112 B

[56] References Cited

U.S. PATENT DOCUMENTS

| | | | |
|---|---|---|---|
| 2,673,848 | 3/1954 | Papesch | 260/256 |
| 4,156,081 | 5/1979 | Singh et al. | 544/271 |
| 4,230,805 | 10/1980 | Singh et al. | 435/188 |
| 4,262,089 | 4/1981 | Singh et al. | 435/7 |
| 4,401,765 | 8/1983 | Craig et al. | 436/533 |

FOREIGN PATENT DOCUMENTS

| | | | |
|---|---|---|---|
| 25722 | 3/1981 | European Pat. Off. | 435/68 |
| 1050244 | 6/1981 | European Pat. Off. | 435/68 |
| 44441 | 1/1982 | European Pat. Off. | 435/68 |
| 197810 | 10/1978 | Fed. Rep. of Germany | 435/7 |

OTHER PUBLICATIONS

Boettscher, Irmgard et al., "Permanent Production of . . . Napten Spec." *Chemical Abstracts* vol. 91, No. 82053x, 1980.
Kohler, et al., Nature, 256, 495, (1975), Current Topics in Microbiology and Immunology, vol. 81, F. Melchers, M. Potter, and N. Warner, Ed., Springer–Verlag, 1978.
Monoclonal Antibodies, R. Kennett, T. McKearn and K. Bechtol, Ed., Plenum Press 1980.
Mudgett–Hunter et al., Federal Proceedings, 39,928, (1980).
Makela et al., Scand. J. Clin. Lab. Invest., 41,75, (1981).

*Primary Examiner*—Lionel M. Shapiro
*Assistant Examiner*—Robin L. Teskin
*Attorney, Agent, or Firm*—George A. Frank

[57] ABSTRACT

Monoclonal antibodies to theophylline having 5% or less cross-reactivity with caffeine and the continuous hybrid monoclonal cell lines for their production are provided. These antibodies are useful in a particle-enhanced turbidimetric inhibition immunoassay for theophylline.

3 Claims, 3 Drawing Figures

HYBRIDOMA CELL LINES AND MONOCLONAL ANTIBODIES TO THEOPHYLLINE

CROSS REFERENCE TO RELATED APPLICATION

This application is a continuation-in-part of application Ser. No. 393,680, filed June 30, 1982, now abandoned.

TECHNICAL FIELD

This invention relates to hybrid cell lines (lymphocyte hybridomas) for the production of monoclonal antibody to theophylline (1,3-dimethylxanthine), to the homogeneous, monospecific antibodies, and their use in immunoassays for theophylline.

BACKGROUND ART

In 1975, Kohler and Milstein reported the establishment of a continuous hybrid cell line (hybridoma) derived by the fusion of murine myeloma cells to spleen cells from an immunized mouse which secreted monoclonal antibody to sheep red blood cells; Nature, Volume 256, 495 (1975). Numerous publications have since appeared describing the production of monoclonal antibodies to other antigens and haptens. See, for example, Current Topics in Microbiology and Immunology, Volume 81, F. Melchers, M. Potter, and N. Warner, ed., Springer-Verlag, 1978, and references contained therein; and Monoclonal Antibodies, R. Kennett, T. McKearn and K. Bechtol, ed., Plenum Press, 1980, and references contained therein.

Although the general technique of producing hybridomas is well known and understood, there are still considerable difficulties involved in producing and selecting a hybridoma cell line secreting antibody having a given set of desired properties.

European Patent Application No. 25,722, published Mar. 25, 1981, discloses the production of a monoclonal antibody to a human T-lymphocyte cell surface antigen.

The production of monoclonal antibodies to the cardiac glycoside, digoxin, has been reported in Federation Proceedings, Volume 39, 928 (1980) and in Scand. J. clin. Lab. Invest., Volume 41, 75 (1981).

There is a rapidly expanding market for clinical diagnostic assays which can be used to monitor the levels of various therapeutic drugs in body fluids. The antiasthmatic agent, theophylline, is a drug whose therapeutic range is very narrow. An immunoassay for theophylline requires a highly specific antibody because of the occurrence in body fluids of other xanthines which are closely related structurally to theophylline and which, if recognized by the anti-theophylline antibody, would produce an erraneous value for the theophylline concentration in the fluid being analyzed. Theophylline is 1,3-dimethylxanthine while four of the most commonly encountered cross-reactive xanthines are: caffeine, 1,3,7-trimethylxanthine; theobromine, 3,7-dimethylxanthine; xanthine; and hypoxanthine. The most frequently encountered xanthine which is a potential cross-reactant is caffeine which is ubiquitous in popular beverages. It is also a metabolite of theophylline in neonates in whom the level of caffeine may approach the level of theophylline. It is thus essential that anti-theophylline antibodies employed in a diagnostic immunoassay for theophylline not cross-react with caffeine.

Theophylline and other compounds of formula weight generally less than 1000 are not immunogenic unless coupled to a carrier which is itself immunogenic; see, for example, H. N. Eisen, Immunology, Harper and Row, 1980. Such compounds are called haptens and there are numerous methods known in the art for coupling them to carriers in order to render the hapten immunogenic.

The choice of carrier and the site of attachment of the hapten to the carrier are known to influence the immunogenicity of the hapten-carrier conjugate as well as the specificity of the antibodies produced. See, for example, B. F. Erlanger, Methods in Enzymology, Volume 70, 85 (1980).

U.S. Pat. No. 4,156,081, issued May 22, 1979, to Singh, et al. describes the synthesis of 3-substituted theophylline derivatives and their use as immunogens to produce antibodies to theophylline which do not cross-react with caffeine. They do, however, cross-react with 1-methylxanthine. Furthermore, there are large quantities of antiserum needed for a commercial immunoassay and their production by animal immunization is slow, laborious and not readily reproducible from animal-to-animal or even bleed-to-bleed in the same animal.

European Patent Application No. 44,441, published Jan. 27, 1982, discloses the production of monoclonal antibodies to drugs. It does not disclose a monoclonal antibody to theophylline which substantially lacks cross-reactivity with caffeine.

DISCLOSURE OF THE INVENTION

The cell lines of this invention are three continuous hybrid monoclonal cell lines, each capable of producing a unique monoclonal antibody to theophylline. The cell lines are hybrids of a spleen cell from a mouse immunized with an 8-substituted theophylline-carrier conjugate (immunogen) and a mouse myeloma cell. Each of the antibodies of this invention exhibits less than 5% cross-reactivity with caffeine when evaluated in a particle-enhanced turbidimetric inhibition immunoassay for theophylline (described in copending patent application Ser. No. 315,922, filed Oct. 28, 1981 and hereby incorporated by reference) and each exhibits variable but low cross-reactivity with other xanthines encountered in body fluids. The use of these monoclonal antibodies in immunoassays for theophylline, especially in a particle-enhanced turbidimetric inhibition immunoassay, is also contemplated.

DESCRIPTION OF THE INVENTION

Figure 1:
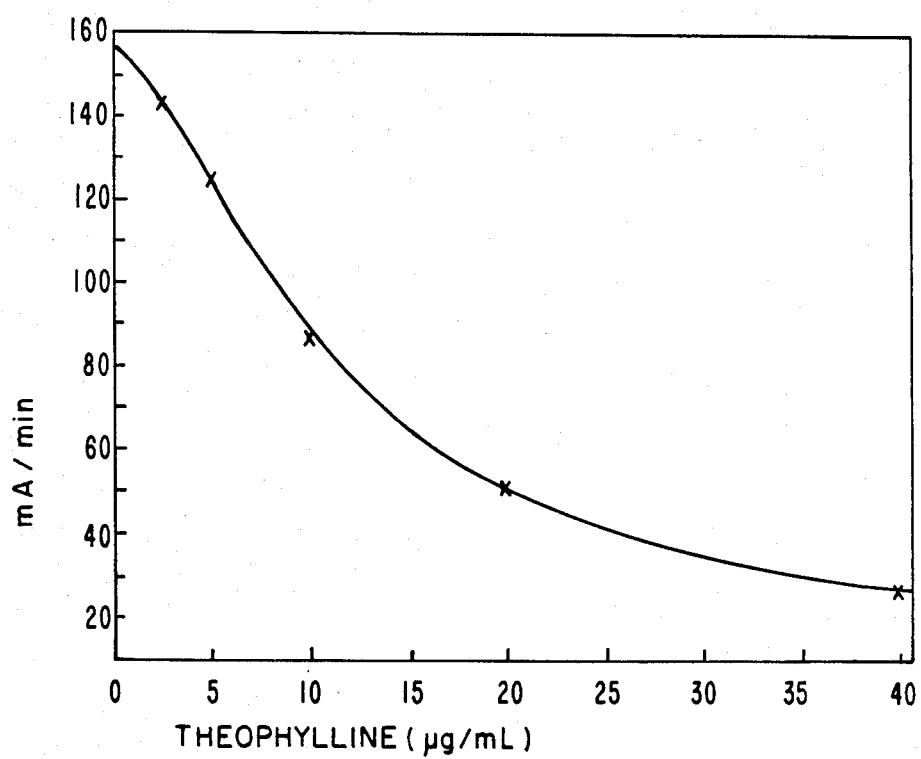
FIGS. 1, 2 and 3 are standard assay curves generated in particle-enhanced turbidimetric inhibition immunoassays utilizing monoclonal antibodies to theophylline produced by the cell lines 30/15, 17/14, and 61/7, respectively.

Monoclonal antibodies are produced by fusing spleen cells from a mouse, immunized with the antigen or hapten of interest, in this case theophylline, to a mouse myeloma cell line. When the compound to which the monoclonal antibodies are raised is a hapten, it is necessary to first conjugate the hapten to a high molecular weight carrier to obtain an immunogen. Such carriers include proteins, polysaccharides, and various latex particles. For the purposes of the present invention, theophylline is conjugated through its 8-position to amino groups on keyhole limpet hemocyanin (KLH)

using carbodiimide as a coupling agent to yield theophylline-8-KLH.

As a matter of practice, several immunizations can be performed at intervals over the course of several weeks to months. The immunized animal such as mouse is bled at the time of each injection and the serum assayed for presence of the desired antibody. Any suitable assay can be used; radioimmunoassays or enzyme-linked immunosorbent assays are frequently employed. When antibody is detectable in the serum, the animal is sacrificed and the spleen is removed aseptically for fusion.

Several different murine (mouse) myeloma cell lines are known to be suitable as fusion partners. The features of some of these cell lines are described in Current Topics in Microbiology and Immunology, referred to above. Generally, it is preferable to choose a myeloma line which does not secrete an immunoglobulin product of its own.

Fusion is carried out most commonly by using polyethylene glycol as a fusion promoter. Other fusion promoters such as Sendai virus can also be used. The ratio of spleen cells to myeloma cells can vary, most often a ratio of 5–10:1 is used.

After fusion, the cells are diluted and cultured in a selective medium such as hypoxanthine aminopterin thymidine (HAT). The unfused spleen cells undergo a finite member of divisions and then die; and unfused myeloma cells will die, because the mutation which they carry in the hypoxanthine guanine phophoribosyl transferase (HGPRT) gene does not permit them to survive on HAT medium. The suspension of hybrid and unfused cells is diluted prior to culturing so as to limit the number of cells per vessel. Usually, they are diluted to the point at which there are 1–5 cells per well of a microtiter plate.

When cell growth becomes visible, the culture supernatant is tested for the presence of the desired antibody by solid-phase radioimmunoassay (RIA) or any other appropriate assay. The cells from wells producing antibody of interest are then cloned in soft agar or by limiting dilution to insure monoclonality.

Large volumes of antibody can then be obtained either by growing the hybridoma in vitro and harvesting the culture supernatant, or by injecting the hybridoma cells into mice. Antibodies can be obtained in ascites fluid by injecting the hybridoma cells into the peritoneal cavity of pristane-primed syngeneic or congenic mice. Antibodies can be obtained in the serum by injecting the hybridoma intraveneously. The quantity of antibody per milliliter is variable, usually being lowest in the culture supernatant and highest in ascites fluid.

The monoclonal antibody thus generated can be characterized by its immunoglobulin class and subclass, as well as by its isoelectric focusing pattern. Affinity constants can be obtained and the antibody characterized in terms of its cross-reactions with a panel of related antigens (haptens).

The present invention comprises monoclonal antibodies to theophylline. Three different clonotypes, 30/15, 17/14, and 61/7, were derived by immunization of Balb/c mice with theophylline-8-KLH. All are products of a single fusion. All are of the same heavy and light chain class but each of these clonotypes has a unique isoelectric focusing pattern. All bind theophylline and can be used in immunoassays for the measurement of theophylline. One such immunoassay is a particle-enhanced turbidimetric inhibition immunoassay. None of these clonotypes cross-reacts significantly with caffeine, the major interferent in immunoassays for theophylline and each exhibits low cross-reactivity with other xanthines.

The hybridoma cell lines 30/15, 17/14, and 61/7 were deposited in the American Type Culture Collection, 12301 Parklawn Drive, Rockville, Md. 20852 on Aug. 5, 1982 and were given the ATCC accession numbers HB8152, HB8153, and HB8154, respectively.

The hybridoma cell lines producing the monoclonal antibodies of this invention are hybrids of the mouse myeloma line P3-NSI-1-Ag4-1 (referred to as NS-1) and Balb/c spleen cells. The NS-1 cell line is itself derived from a Balb/c mouse and synthesizes a kappa light chain which, however, is not secreted. NS-1 is available from the Salk Institute Cell Distribution Center, La Jolla, Calif.

The hybridoma cell lines of this invention are hybrids, a fact evidenced by the presence of gene products of both parents in each hybrid clone. These are characterized by the specific antibody which each produces. Each cell line has been shown to behave in a stable fashion for at least one year with respect to the specificity of the antibody produced and other assay performance parameters. The 30/15 line has been re-cloned from frozen material on two occasions; the 17/14 line has been re-cloned from frozen material once. The 61/7 line has not yet been re-cloned.

EXAMPLE 1

Production of Monoclonal Anti-Theophylline Cell Lines

A. Preparation of Theophylline-8-KLH 8-(3-carboxypropyl)-theophylline was synthesized as described in copending patent application Ser. No. 315,922, filed Oct. 28, 1981. 15 mg of this compound was reacted with 7 mg of N-hydroxysuccinimide in 2.0 ml of dimethylformamide at 4° C. for 18 hours. At the end of this time, 200 mg of KLH, dissolved in 15 ml of 0.1M sodium carbonate, pH 8.5, was added. The reaction mixture was stirred for 18 hours at 4° C. Unreacted theophylline was removed by dialysis.

B. Immunization

A Balb/c mouse was injected intraperitoneally with 300 μg of theophylline-8-KLH (prepared as in (A) above) emulsified in 0.3 mL of complete Freund's adjuvant. Three booster injections were given at 21-day intervals as described above. Seven days after the last boost, the mouse was bled and the serum tested for circulating anti-theophylline antibody by solid phase RIA using $I^{125}$-labeled protein A and by a particle-enhanced turbidimetric inhibition immunoassay, described below. The mouse was given a final boost intraperitoneally and four days later the spleen was removed for fusion.

C. Particle-enhanced Turbidimetric Inhibition Immunoassay

This assay was used to screen the mouse serum, as follows: 5 μL of mouse serum was added to a cuvette containing 12.5 μL of theophylline-HSA coated latex particles (described in copending patent application Ser. No. 315,922, filed Oct. 28, 1981), 2.5% (v/v, final concentration) polyethylene glycol 6000, and 0.15M phosphate buffer, pH 7.8, in a total volume of 1 mL. Turbidity due to antibody-mediated aggregation of the latex particles was measured at 340 nm, 37° C., in a recording spectrophotometer. The rate of turbidity formation was 0.2 absorbance units for 5 μL of serum from the mouse whose spleen was subsequently chosen for fusion.

D. Fusion

The spleen was removed aseptically and a single cell suspension prepared. The cells were then fused with NS-1 myeloma cells at a ratio of 5:1 using 0.2 mL of 30% (v/v) polyethylene glycol 1000 in serum-free medium. The fused cells were washed in serum-free medium, suspended in 30 mL of serum-free medium, plated into 96-well microtiter plates (about 50 μL per well) containing feeder layers of mouse peritoneal macrophages.

HAT selection medium was added 18 hours later. After five days, the wells were scanned every other day for the presence of hybrid cell colonies. When hybrids were detected (approximately 2 weeks after fusion), the wells were marked and kept under observation until the cells had grown to the point at which expansion into larger volume was desirable. At this time, the supernatants from the hybrid-containing wells were harvested for screening and the cells were expanded into 24-well plates. After 3 weeks, the hybrids were cultured on HT medium (containing hypoxanthine and thymidine). At this stage and macrophase feeder layers had cleared the cultures of dead cells and debris and their use was discontinued.

E. Screening

The supernatants harvested above were screened for anti-theophylline antibody by solid state RIA. The antigen used in the screening assay was theophylline-8-BSA (20 moles of theophylline per mole of BSA), synthesized as described above for theophylline-8-KLH. The second antibody was $I^{125}$-labeled goat anti-mouse Ig.

A total of 56 positive wells was detected by RIA. These wells were then rescreened using $I^{125}$-labeled protein A. This reagent detects only antibodies of the IgG class. Of the 56 positive supernatants, 28 proved to be of the IgG class, including cell lines 30/15, 17/14, and 61/7.

These 28 supernatants were then screened for their ability to bind free theophylline. Free theophylline (final concentration 10 μg/mL) was incorporated into the solid state RIA; the ability to bind free theophylline was evidenced by a decrease in antibody binding to the immobilized theophylline-8-BSA antigen.

Supernatants were screened in a similar manner for their ability to bind caffeine. In these assays, free caffeine was present at a final concentration of 50 μg/mL. Lack of cross-reactivity with caffeine was evidenced by uninhibited binding of the antibody of this invention to the immobilized theophylline-8-BSA antigen.

Table I shows the results of these assays for the antibodies produced by the three cell lines of interest. The data show that the binding of these antibodies to immobilized theophylline-8-BSA is inhibited by free theophylline but not by 5-times as much free caffeine.

TABLE I

| Monoclonal antibody | Antibody Specificity | | |
|---|---|---|---|
| | CPM Bound $I^{125}$ Labeled Protein A | | |
| | 30/15 | 17/14 | 61/7 |
| Control (no free theophylline) | 1245 | 1195 | 1443 |
| Theophylline added | 800 | 687 | 1134 |

TABLE I-continued

| Monoclonal antibody | Antibody Specificity | | |
|---|---|---|---|
| | CPM Bound $I^{125}$ Labeled Protein A | | |
| | 30/15 | 17/14 | 61/7 |
| Caffeine added | 1316 | 1265 | 1483 |

F. Cloning at Semi-Limiting Dilution

The hybrid cell lines of interest (30/15, 17/14, 61/7) were expanded to sufficient numbers to allow cloning at semi-limiting dilution, that is, at approximately 3 cells/microtiter well. An aliquot of the cells was also viably frozen in liquid nitrogen as a safeguard against loss. Feeder layers of peritoneal macrophages were again used. When acceptable numbers of cells were present in the wells, the supernatants were again screened using the solid phase RIA. Positive wells were selected for expansion and further cloning.

G. Cloning at Limiting Dilution

The wells selected were then cloned at limiting dilution, using strict Poisson statistics. In this case approximately one-third of the wells should show growth and the probability is very high that the cells growing in a given well were the progeny of a single hybridoma cell. When sufficient numbers of cells were present in the wells, the supernatants were again tested for presence of monoclonal antibody. All lines continued to produce the desired antibody.

H. Chain Composition

All monoclonal antibodies derived from cell lines 30/15, 17/14, and 61/7 consisted of gamma heavy chains (subclass 1) and kappa light chains, as determined by double diffusion in agar gel.

EXAMPLE 2

Production of Monoclonal Antibody in Ascites Tumors

In order to produce large amounts of monoclonal anti-theophylline, approximately $10^6$ hybridoma cells were injected intraperitoneally into pristane-primed syngeneic Balb/c mice. Ascites fluid was withdrawn and shown to have high concentrations of anti-theophylline activity by both solid state RIA and a particle-enhanced turbidimetric inhibition immunoassay, as described below.

EXAMPLE 3

Immunoassay for Theophylline

Ascites fluid from 30/15, 17/14, and 61/7-primed mice was used in a particle-enhanced turbidimetric inhibition immunoassay performed on the aca TM discrete clinical analyzer (available from E. I. du Pont de Nemours and Company). 20 μL of a serum-based theophylline calibrator, containing from 0 to 40 μg/mL of theophylline, was automatically injected into an analytical test pack (described in No. Re 29,725, issued Aug. 8, 1978 to Johnson et al., hereby incorporated by reference) in the filling station of the instrument, followed by 4.980 mL of buffer containing 3% (v/v) polyethylene glycol 6000, 0.1% GAFAC RE-610, and 0.15M phosphate, pH 7.8. The pack was automatically warmed to 37° C. 40 μL of theophylline-HSA coated latex particles (described in copending patent application Ser. No. 315,922, filed Oct. 28, 1981) and 50 μL of 750 mM dithioerythritol were added from dimples 2 and 3, respectively, at breaker/mixer I. Anti-theophylline antibody, as sterile-filtered ascites fluid, was added to the pack from dimple 6 at breaker/mixer II (17–50 μL, depending on the cell line). The rate of turbidity formation was measured automatically at 340 nm, approximately 39 seconds after the initiation of the reaction at breaker/mixer II.

Figure 2:
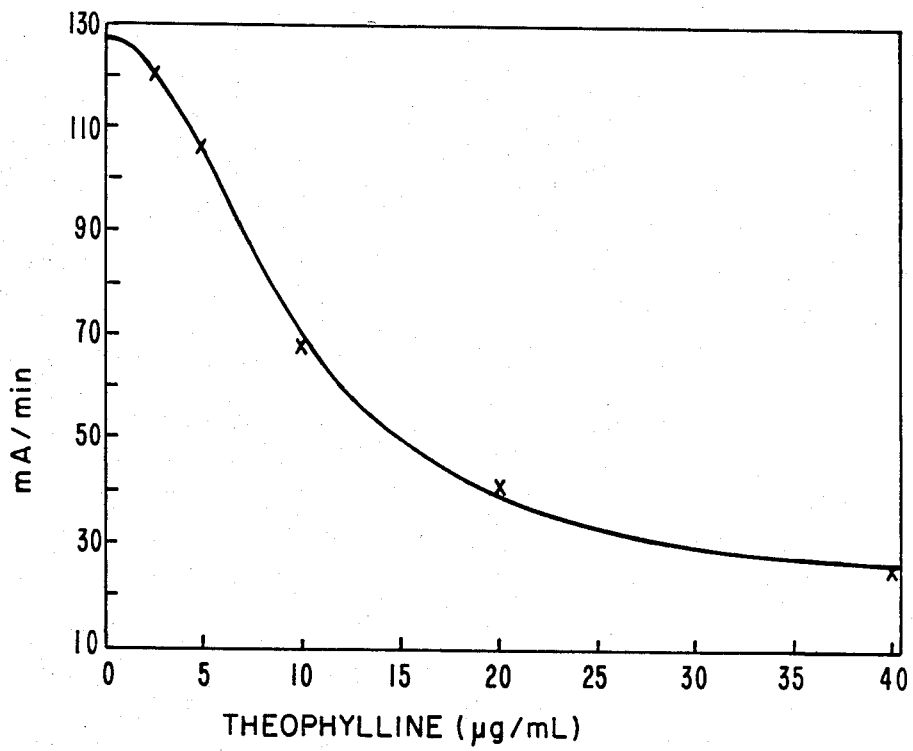
Figure 3:
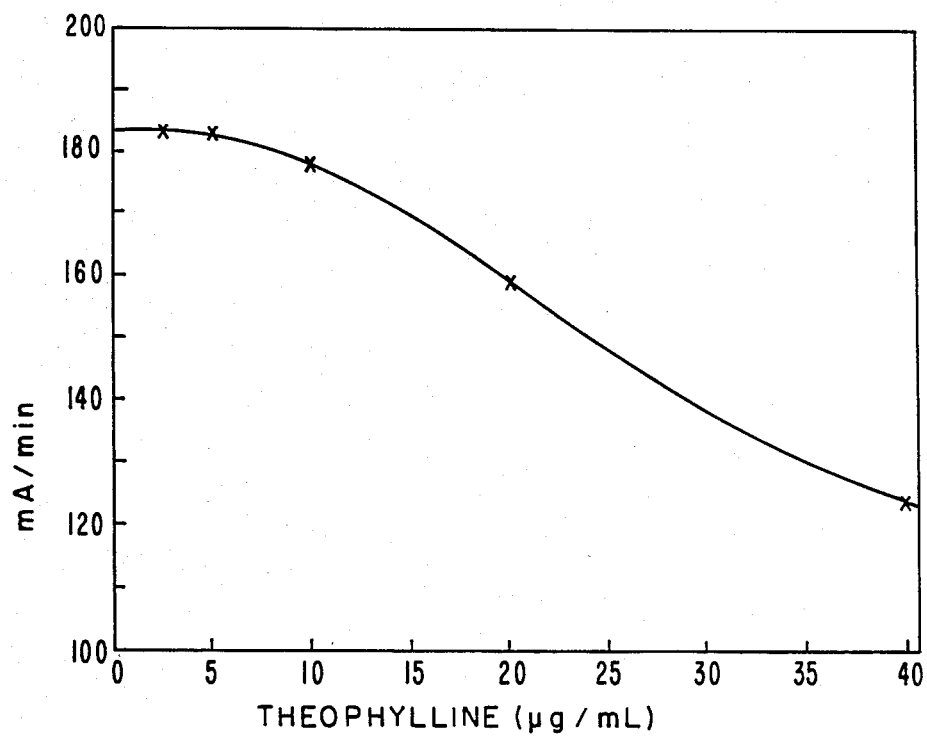

FIG. 1 shows a typical standard curve generated using 28 μL of 30/15 ascites fluid. FIG. 2 shows a typical standard curve generated using 17 μL of 17/14 ascites fluid. FIG. 3 shows a typical standard curve generated using 50 μL of 61/7 ascites fluid.

EXAMPLE 4

Specificity of Cell Lines 30/15, 17/14, and 61/7 for Theophylline

In order to measure theophylline accurately in an immunoassay, the anti-theophylline antibody must exhibit little or no cross-reactivity with other xanthines present in samples. Cross-reactivity is defined as the percentage error in measurement introduced when the material in question is present at a final concentration of 10 μg/mL in a sample containing 10 μg/mL theophylline.

Table II compares the cross-reactivities of 30/15, 17/14, 61/7 with two rabbit antisera, 924P0213 and 904P0518, to caffeine, theobromine, 1,7-dimethylxanthine, 3-methylxanthine, hypoxanthine, and xanthine. The two rabbit antisera were raised to theophylline-8-BSA and are typical of more than ten different pools of rabbit antisera tested.

The monoclonal antibodies of this invention produced by cell lines 30/15, 17/14, and 61/7 are specific for theophylline and are superior to the polyclonal rabbit antibodies.

TABLE II

| | Cross-Reactivity (% Error) | | | | |
| | Monoclonal | | | Rabbit | |
| Compound | 30/15 | 17/14 | 61/7 | 924P0213 | 904P0518 |
| --- | --- | --- | --- | --- | --- |
| Caffeine | 5 | 5 | 5 | 40 | 25 |
| Theobromine | 5 | 30 | 25 | — | — |
| 1,7-Dimethyl-xanthine | 10 | 25 | 10 | — | — |
| 3-Methylxanthine | 5 | 5 | 5 | — | — |
| Hypoxanthine | 5 | 5 | 10 | — | — |
| Xanthine | 5 | 5 | 5 | — | — |

I claim:

1. Mouse monoclonal IgG isotype antibody to theophylline having 5% or less cross-reactivity with caffeine wherein the hybrid continuous cell line producing said antibody is a hybrid of a spleen cell from a mouse immunized with an 8-substituted theophylline-carrier conjugate and a mouse myeloma cell line.

2. The monoclonal antibody of claim 1 having 30% or less cross-reactivity with theobromine and 5% or less cross-reactivity with 3-methylxanthine.

3. The monoclonal antibody of claim 1 wherein the conjugate is theophylline-8-KLH.

* * * * *